United States Patent [19]
Wang

[11] Patent Number: 5,840,879
[45] Date of Patent: Nov. 24, 1998

[54] REAGENTS AND SOLID SUPPORTS FOR IMPROVED SYNTHESIS AND LABELING OF POLYNUCLEOTIDES

[76] Inventor: Edge R. Wang, 18886 Sydney Cir., Castro Valley, Calif. 94546

[21] Appl. No.: 761,711

[22] Filed: Dec. 6, 1996

[51] Int. Cl.$^6$ .......................... C07H 21/00; C07H 21/02; C07H 21/04
[52] U.S. Cl. .................................. 536/25.32; 536/25.33; 536/25.34; 536/26.6; 536/26.7; 536/26.74; 536/26.8; 536/27.6; 536/27.81; 536/28.5; 536/28.53; 558/70; 560/19; 560/21; 560/22; 564/123; 568/306; 568/325
[58] Field of Search .............................. 536/25.32, 25.33, 536/25.34, 26.6, 26.7, 26.74, 26.8, 27.6, 27.81, 28.5, 28.53; 558/70

[56] References Cited

U.S. PATENT DOCUMENTS

| | | | |
|---|---|---|---|
| 4,908,453 | 3/1990 | Cocuzza et al. | 548/113 |
| 5,141,813 | 8/1992 | Nelson | 428/402 |
| 5,231,191 | 7/1993 | Woo et al. | 549/220 |
| 5,359,100 | 10/1994 | Urdea et al. | 552/105 |
| 5,401,837 | 3/1995 | Nelson | 536/25.32 |
| 5,451,463 | 9/1995 | Nelson et al. | 428/402 |

FOREIGN PATENT DOCUMENTS

| | | |
|---|---|---|
| 0523557 | 1/1993 | European Pat. Off. . |
| 0573848 | 12/1993 | European Pat. Off. . |
| 9202638 | 2/1992 | WIPO . |
| 9521266 | 10/1995 | WIPO . |
| 9614330 | 5/1996 | WIPO . |
| 9631841 | 10/1996 | WIPO . |
| 9719106 | 5/1997 | WIPO . |

OTHER PUBLICATIONS

Lyttle et al., "A New Universal Linker for Solid Phase DNA Synthesis," *Nucleic Acids Research*, 24(14), 2793–2798 (1996).

Berlin et al., "Multiple Non–Radioactive Labeling of Oligonucleotides," *Nucleic Acids (18th) Symposium Series*, 25, 85–86 (1991); *Chem. Abstr.*, 118(1), p. 778, Abstr. No. 7300m (Jan. 4, 1993); only Abstract supplied.

Huynh et al., "Synthesis of Cholesteryl Supports and Phosphoramidites Containing a Novel Peptidyl Linker for Automated Synthesis of Triple–Helix Forming Oligonucleotides," *Nucleic Acids Symposium Series*, 29, 19–20 (1993) *Chem. Abstr.*, 120(15), p. 1098, Abstr. No. 192,171x (Apr. 11, 1994); only Abstract supplied.

Endo et al., A Novel Phosphoramidite for the Site–Selective Introduction of Functional Groups into Oligonucleotides via Versatile Tethers, *Tetrahedron Letters*, 35(32), 5879–5882 (Aug. 8, 1994).

Wenniger et al., "Synthesis and Enzymatic Studies of Modified Oligonucleotides with Abiological Monomers Units," *Nucleosides & Nucleotides*, 16(5–6), 761–768 (May/Jun. 1997).

Goodman et al., "A Template–Induced Incipient Collagen––like Triple–Helical Structure," *J. Am. Chem. Soc.*, 118(21), 5156–5157 (May 29, 1996).

Nelson et al., "A New and Versatile Reagent for Incorporation Multiple Primary Aliphatic Amines Into Synthetic Oligonucleotides," *Nucleic Acids Research*, 17(18), 7179–7186 (Sep. 25, 1989).

Agrawal et al., "Efficient Methods for Attaching Non–Radioactive Labels to the 5' Ends of Synthetic Oligonucleotides," *Nucleic Acids Research*, 14(15), 6227–6245 (Aug. 11, 1986).

Korshun et al., "Reagents for Multiple Non–Radioactive Labelling of Oligonucleotides," *Synthetic Communications*, 26(13), 2531–2547 (1996).

*Primary Examiner*—Marian C. Knode
*Assistant Examiner*—L. Eric Crane
*Attorney, Agent, or Firm*—Richard Aron Osman

[57] ABSTRACT

The invention provided methods and compositions for oligonucleotide synthesis and labeling. The subject compounds have either rigid ring or long linear linker structures and provide enhanced coupling efficiencies over prior art labeling reagents because of lack of stereo hindering and/or provide more convenient and cost-effective syntheses. These novel linkers also contain a base labile structure which provides: labeling at 3' end with regular solid supports, cleaving under mild conditions, and achieving higher yield because of the complete cleavage and higher purity because the mild conditions will not bring down the impurities on the solid support. When used in a solid support pre-attached with either a nucleotide for unlabeled oligonucleotide synthesis, or a label for 3' end labeled oligonucleotide synthesis, or an alternate structure to use as an universal support, these linkers provide solid supports requiring only mild cleavage conditions.

9 Claims, No Drawings

REAGENTS AND SOLID SUPPORTS FOR IMPROVED SYNTHESIS AND LABELING OF POLYNUCLEOTIDES

FIELD OF THE INVENTION

The field of the invention is reagents for solid phase synthesis and labeling of polynucleotides.

BACKGROUND OF THE INVENTION

Non-radioisotopic labeling of oligonucleotide has found wide applications in nucleic acid analysis, such as DNA sequencing, mapping, DNA/RNA blotting, and fluorescence quenching assays. The ability to label an oligonucleotide at any selected position along the sequence (5' end, 3' end and the middle of the sequence) and multi-labeling is particularly advantageous. Multi-labeling effects not only signal amplification but also finds application in DNA sequencing with energy transfer dyes (World Patent WO95/21266) and nucleic acid analysis with homogenous PCR assays (World Patent WO92/02638). While currently available technologies make such labeling possible by using labeled phosphoramidites or labeled solid supports, they suffer several drawbacks. First, these phosphoramidites have short linear backbones: two or three carbons between the two hydroxyl groups which serve as coupling sites, one bond to the amidite group for oligonucleotide chain elongation and the other protected with dimethoxytrityl (DMT) for next coupling. This short distance lowers the coupling efficiency. Second, the distance between the label and the coupling site is short which also contributes to the lower coupling efficiency. Third, these phosphoramidites can not be used for labeling at the 3' end with conventional solid supports. In particular, since conventional supports have the first base pre-attached, labeling results in label deposition at the second position from the 3' end. Therefore, special solid supports are required. Finally, by using these phosphoramidites and solid supports, the cleavage conditions have to be very strong, typically ammonium hydroxide, which decompose some many popular labels such as rhodamine dyes.

RELEVANT LITERATURE

Relevant Literature includes Nelson (1992) U.S. Pat. No. 5,141,813, Nelson et al. (1995) U.S. Pat. No. 5,451,463, and Nelson (1995) U.S. Pat. No. 5,401,837; Woo et al. (1993) U.S. Pat. No. 5,231,191; and Lyttle et al. (1996) Nucleic Acids Research, 24 (14) 2793–2798. Urdea et al. (1994) U.S. Pat. No. 5,359,100 describes labeling reagents which facilitate the production of branched oligonucleotide. Background information is provided in Caruthers et al. (1992) Methods Enzymology 211, 3–20 and Oligonucleotides and Analogs, A Practical Approach, IRL Press, Oxford, 1991. Ed. F. Eckstein.

SUMMARY OF THE INVENTION

The compounds of the present invention overcome the prior art shortcomings by having either rigid ring or long linear linker structures. Such structures provided enhanced coupling efficiencies over prior art labeling reagents because of lack of stereo hinderance and/or provide more convenient and cost-effective syntheses. These novel linkers also contain a base labile structure which provides at least three advantages: (1) labeling at 3' end with regular solid supports, (2) cleaving under mild conditions, and (3) achieving higher yield because of the complete cleavage and higher purity because the mild conditions will not bring down the impurities on the solid support. When used in a solid support pre-attached with either a nucleotide for unlabeled oligonucleotide synthesis, or a label for 3' end labeled oligonucleotide synthesis, or an alternate structure to use as an universal support, these linkers provide solid supports requiring only mild cleavage conditions, which is important for avoiding label decomposition. Furthermore, when conventional cleavage conditions are used, such as ammonium hydroxide, the compound effect faster cleavage.

This invention includes four groups of compounds of the following general formulas:

Group 1:

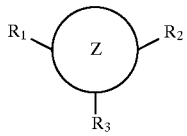

where

Z is ring structure containing 3–8 C, O, N, and/or S atoms and hydrogen;

$R_1$ is a label or a protecting group attached to the ring through a linker arm;

$R_2$ is a label or a protecting group attached to the ring through a linker arm;

$R_3$ is a coupling group or solid support attached to the ring through a linker arm.

Group 2:

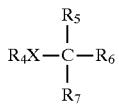

where $R_4$ comprises a label attached to the carbon atom through a functional group;

$R_5$ is a label or a protecting group attached to the carbon atom through a linker arm;

$R_6$ is a coupling group or solid support attached to the ring through a linker arm;

$R_7$ is H or lower alkyl group;

X is NH, O or S.

Group 3:

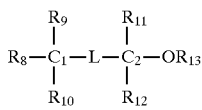

where $R_8$ is a group containing an N, O, or S atom;

$R_9$ is a coupling group or solid support attached Cl through a linker arm;

$R_{10}$, $R_{11}$ and $R_{12}$ are H or lower alkyl groups;

$R_{13}$ is a protecting group;

L is a linker arm containing 0 to 4 C, O, S or N atoms. and Group 4:

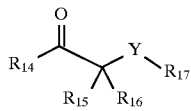

where

R$_{14}$ is a nucleoside moiety;

R$_{15}$, R$_{16}$ are H or lower alkyl groups;

R$_{17}$ is a coupling group or solid support attached to the C through a functional group, Y;

Y is NH, S or O.

The subject structures also provide reagents and solid supports for multi-labeling either in one step or multi-steps. For example, in one-step multi-labeling, the reagents contain two or more labels to incorporate the labels into the oligonucleotide in one coupling. In multi-step multi-labeling, the reagents containing one or more labels are repeatedly incorporated onto the oligonucleotide sequence. This approach may be used to make energy transfer dye labeled oligonucleotides having application, inter alia, in oligonucleotide sequencing, and multi-labeled oligonucleotides for signal amplification. Furthermore, providing protecting groups at a plurality of the three side chains (e.g. the label, DMT and controlled-pore glass, or CPG, side chains), permits the generation of branching nucleic acids.

Another aspect of the invention is related to universal supports, i.e. supports which may be used as starting points for oligonucleotide synthesis regardless the nucleoside species at the 3' end of the sequence. This type of support has broad application because only one such support is needed to carry out the oligonucleotide synthesis regardless of what base is at the 3' end. This simplifies synthetic strategy and reduces the number of required reagents in inventory. Whereas, other universal supports require cleavage under conditions supplemental to ammonium hydroxide, (e.g. Lyttle et al., supra) making them less useful in many conventional syntheses where ammonium hydroxide is used as cleavage regent, the universal support of the present invention permit the use of ammonium hydroxide for cleavage. Additionally, the invention provides reagents for converting conventional supports to universal supports. For conventional synthesis or universal support based synthesis, the subject compounds effect faster cleavage, higher yield and purity.

DETAILED DESCRIPTION OF SPECIFIC EMBODIMENTS

The invention is exemplified with generic structures incorporating functional groups including protecting groups, organic linker arms, labels, coupling groups and solid supports. Generally, the selected functional groups are compatible with the reagents, solvents, reaction conditions and equipment used in conventional automated oligonucleotide synthesis. For example, a wide variety of labels may be used, including directly detectable labels such as dyes, such as luminescers and fluorescers (e.g. rhodamine, lanthanide-based dyes, etc.) and indirectly detectable labels such as enzymes and haptens, including digoxigenin, biotin, etc. Similarly, any of a variety of known protecting groups, including amine protecting groups like Fmoc (9-fluorenylmethyloxycarbonyl), BOC (butyloxycarbonyl), etc. and hydroxyl protecting groups such as DMT, monomethoxytrityl (MMT), LEV (Levulinicyl), etc., coupling groups such as a phosphoramidite, preferably a 2-cyanoethyl phoshoramidite, and solid supports such as CPG (controlled pore glass), polystyrene, etc., may be used. The organic linker arms effect separation of the label or protected functional group used for label coupling, the protected hydroxyl group and the solid support or nucleotide coupling group, sufficient to provide acceptable coupling efficiencies and label signal. Preferred linker arms are described for each generic structure. Unless otherwise stated, descriptions of common groups, e.g. linkers, protecting groups, etc., apply to each generic structures.

Group 1 compounds of the invention have the following general structure:

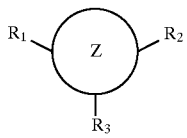

where

Z is ring structure containing 3–8 C, O, N, and/or S atoms and hydrogen, and Z is independently substituted at at least three ring positions with R$_1$, R$_2$ and R$_3$;

R$_1$ is a label or a protecting group attached to the ring through a linker arm;

R$_2$ is a label or a protecting group attached to the ring through a linker arm;

R$_3$ is a coupling group or solid support attached to the ring through a linker arm.

The ring structure, Z, may be substituted or unsubstituted, aromatic, nonaromatic or complex, homo or hetero cyclic, bicyclic, or multicyclic. Preferred ring structures are 5- or 6-membered nonaromatic ring structures comprising two or fewer noncarbons atoms, more preferably no noncarbon atoms, in the ring.

R$_1$ comprises a linker arm and a label-coupling group which is either further coupled to a label or label precursor, or is protected with a protecting group. Frequently, the linker arm is coupled to the ring structure through a functional group such as an amine. A wide variety linker arms can be used. Typically, the linker will be from 0 to 20, preferably 0 to 8, atoms in length, largely depending on length of R$_2$ and R$_3$ and the nature of the label(s) and protecting groups. Preferred linkers are primarily hydrocarbon and highly stable to oligonucleotide synthesis conditions. In one preferred embodiment, the linker arm has the structure LX(CH$_2$)$_n$CONH—, where L is a label or protecting group, X is a label-coupling group such as —NH—, and n is an integer from 0 to 20, preferably from 0 to 8. Preferred labels are described above and preferred protecting groups depend on the nature of R$_1$, particularly the nature of the label coupling group. For example, where the label coupling group is an amine, Fmoc is a preferred protecting group.

R$_2$ comprises a linker arm coupling the ring structure to a protecting group, usually a hydroxyl protecting group, or a second label, which may be the same as or different from any label of R$_1$. Again, a wide variety of linker arms can be used. Typically, the linker will be from 0 to 20, preferably 0 to 8, atoms in length, largely depending on length of R$_1$ and R$_3$ and the nature of the label(s) and protecting groups. Preferred linkers are primarily hydrocarbon and, except for the selective cleavability of the protecting group, if present, are highly stable to oligonucleotide synthesis conditions. In one preferred embodiment, the linker arm has the structure LX(CH$_2$)$_n$CONH— where L is a label or protecting group and n is an integer from 0 to 20, preferably from 0 to 8. Preferred protecting groups include DMT, MMT, LEV and the like.

$R_3$ comprises a linker arm coupling the ring structure to a coupling group or a solid support. Frequently, the linker arm is coupled to the ring structure through a cleavable bond such as an ester bond. A wide variety linker arms can be used. Except for the selective cleavability of the cleavable bond, preferred linkers are highly stable to oligonucleotide synthesis conditions. In one preferred embodiment, the linker arm has the structure M-diglycolate moiety, where M is a solid support or a coupling group such as phosphoramidite. Preferred supports are described above and coupling groups depend on the desired application of the compound, particularly the nature of the label coupling group.

In one particular embodiment, $R_1$ is a linker arm and a fluorescence label, $R_2$ a linker arm and a DMT group and $R_3$ linker arm and a phosphoramidite group while the linker arm for $R_3$ is base labile. This labeled and protected phosphoramidite molecule can be used for labeling 3' end of an oligonucleotide using any of the four regular DNA synthesis supports or an universal support. When $R_3$ is a linker arm and solid support (CPG, polystyrene or other organic/inorganic polymers), it provides a support for 3' labeling.

In another particular embodiment, $R_1$ is a linker arms and DMT, $R_2$ a linker arms and DMT (or LEV) and $R_3$ a linker arm and a phosphoramidite group, it provides a reagent for branching the oligonucleotide. When $R_3$ is not a base labile linker arm, this provides a reagent for labeling in the middle of the sequence or multi-labeling. When $R_3$ is a linker arm and solid support (CPG, polystyrene or other organic/inorganic polymers), it provides a support for branching at 3' end.

In yet another particular embodiment, $R_1$ is a linker arm and a label, $R_2$ is a linker arm and a label (same or different from $R_1$ label), $R_3$ a linker arm and a phosphoramidite group. This embodiment provides a reagent for multi-labeling for use in signal amplification and/or energy transfer. When $R_3$ is a linker arm and solid support (CPG, polystyrene or other organic/inorganic polymers), it provides a support for 3' multi-labeling.

Group 2 compounds have the following general structure:

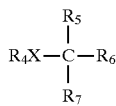

where $R_4$ is a label attached to the central carbon atom through a functional group;

$R_5$ is a label or a protecting group attached to the central carbon atom through a linker arm;

$R_6$ is a coupling group or solid support attached to the central carbon atom through a linker arm;

$R_7$ is H or lower alkyl group;

X is a functional group selected from NH, O or S.

The functional group, X, is joined directly to both the central carbon atom and $R_4$. This design permits more efficient and/or less expensive synthesis as compared with compounds imposing a linker between the functional group and the central carbon atom. For example, many compounds of Group 2 permit the use of inexpensive starting materials such as serine for synthesis. In a preferred embodiment, X is NH.

$R_4$ comprises a label or label precursor, or a protecting group protecting the functional group or a label-coupling group joined thereto. The label or label precursor may be coupled directly to the functional group or through a linker arm.

$R_5$ and $R_6$ are as described for $R_2$ and $R_3$, above. $R_7$ is generally H, but may be any other group which does not interfere with coupling or signal efficiencies of the compound.

In one particular embodiment, $R_4$ is a linker arm and a fluorescent label, $R_5$ a linker arm and a DMT group, $R_6$ a base labile linker arm and a phosphoramidite group, and $R_7$ H. This labeled and protected phosphoramidite molecule can be used for labeling the 3' end of an oligonucleotide using any of the four conventional DNA synthesis supports or an universal support. When $R_6$ is not a base labile linker arm, this provides a reagent for labeling in the middle of the sequence or multi-labeling. When $R_6$ is a linker arm and solid support (CPG, polystyrene or other organic/inorganic polymers), it provides a support for 3' labeling.

In another particular embodiment, $R_4$ is a linker arm and a label, $R_5$ is a linker arm and a label (same or different from $R_1$ label), $R_6$ a linker arm and a phosphoramidite group, and $R_7$ H, it provides a reagent for multi-labeling. When $R_6$ is a linker arm and solid support (CPG, polystyrene or other organic/inorganic polymers), it provides a support for 3' multi-labeling.

Group 3 compounds have the following general structure

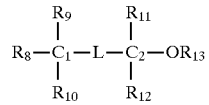

where $R_8$ is a group containing N, O, or S atom(s);

$R_9$ is a coupling group or solid support attached to C1 through a linker arm;

$R_{10}$, $R_{11}$ and $R_{12}$ are H or lower alkyl groups;

$R_{13}$ is a protecting group;

L is a linker arm containing 0 to 4 C, O, S or N atoms.

$R_8$ comprises a good leaving group, preferably comprising multiple halogen substituents.

$R_{13}$ and $R_9$ are as described for $R_2$ and $R_3$, above. $R_{10}$, $R_{11}$ and $R_{12}$ are generally H, but may be any other group which does not interfere with coupling or signal efficiencies of the compound.

In one particular embodiment, $R_8$ is $CF_3CONH$, $R_9$ CPG, $R_{10}$, $R_{11}$, $R_{12}$ H, L is a single bond, and $R_{13}$ DMT. It provides a universal support suitable for ammonium hydroxide cleavage.

Group 4 compounds have the following general structure:

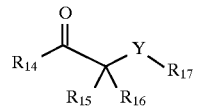

where $R_{14}$ is a nucleoside moiety;

$R_{15}$, $R_{16}$ are H or lower alkyl groups;

$R_{17}$ is a coupling group or solid support attached to the C through a linker arm;

Y is NH, S or O.

The nucleoside moiety, $R_{14}$, may comprise a ribonucleoside, deoxyribonucleoside or modifications/derivatives thereof. In a preferred embodiment, $R_{14}$ is a ribo- or deoxyribonucleoside moiety.

$R_{15}$ and $R_{16}$ are generally H, but may be any other group which does not interfere with coupling or signal efficiencies of the compound. $R_{17}$ is as describe for $R_3$ above. In one particular embodiment, $R_{14}$ is a thymidine, $R_{15}$, $R_{16}$ H, $R_{17}$ OCOCH$_2$OCH$_2$CONH—CPG, and Y is O. It provides a universal solid support for regular oligonucleotide synthesis while cleavage is fast and can be done under mild conditions to give higher yield and purity.

The following examples are offered by way of illustration and not by way of limitation.

EXAMPLES

Synthesis of Compound 1 (Table I)

4.3 g of 1,3,5 cyclohexane tricarboxylic acid (20 mmole) was dissolved in DMF (dimethylformamide). A DMF solution of 6.08 g of Fmoc-1,6-hexanediamine (20 mmole), 1.35 g of 1-hydroxybenzotriazol (10 mmole), 3.79 g of (2-(1H-benzotriazol-1-yl)-1,1,3,3-tetramethyluronium hexafluorophosphate (HBTU) (20 mmole), and 3.88 g of diisopropylethylamine (30 mmole) was added dropwise under Ar gas while stirring. The mixture was stirred for 4 h at room temperature. The solvent then was evaporated and dichloromethane was added to dissolve. The product was purified by silica gel chromatography. Appropriate fractions were combined and solvent was removed under reduced pressure. The product was dried under vacuum.

Synthesis of Compound 2 (Table I)

1.53 g of ethanolamine (25 mmole) was dissolved in DMF. A DMF solution of 5.37 g of 1 (10 mmole), 0.67 g of 1-hydroxybenzotriazol (5 mmole), 1.89 g of (2-(1H-benzotriazol-1-yl)-1,1,3,3-tetramethyluronium hexafluorophosphate (HBTU) (10 mmole), and 1.94 g of diisopropylethylamine (15 mmole) was added dropwise under Ar gas while stirring. The mixture was stirred for 4 h at room temperature. The solvent then was evaporated and dichloromethane was added to dissolve. The product then was purified by silica gel chromatography. Appropriate fractions were combined and solvent was removed under reduced pressure. The product was dried under vacuum.

Synthesis of Compound 3 (Table I)

4.36 g of Compound 2 (7 mmole) was dissolved in pyridine and was added with 2.13 g of DMT-Cl solution in pyridine dropwise under Ar gas flow. The mixture was stirred for 48 h at room temperature. The solvent was removed under reduced pressure and the product was dissolved in dichloromethane. The product then was purified by silica gel chromatography. Appropriate fractions were combined and solvent was removed under reduced pressure. The product was dried under vacuum.

Synthesis of Compound 4 (Table I)

5 g of Compound 3 was dissolved in 20% piperidine in DMF. The solution was stirred at room temperature for 2 h. The solvent was then removed and the product was dissolved in dichloromethane and purified on silica chromatography. Appropriate fractions were pooled and dried under reduced pressure.

Synthesis of Compound 5 (Table I)

72 mg of Compound 4 (0.1 mmole) was dissolved in DMF. 53 mg of TMR-NHS (tetramethylrhodamine N-hydroxysuccinimide) ester (0.1 mmole) and 30 mg of triethylamine (0.3 mmole) were added. The mixture was stirred at room temperature for 16 h and the solvent was removed. The product was dissolved in dichloromethane and purified on silica chromatography. Appropriate fractions were pooled and dried under reduced pressure.

Synthesis of Compound 6 (Table II)

57 mg of Compound 5 (50 $\mu$mole) was dissolved in dichloromethane and 4.5 mg of triethylamine (45 $\mu$mole) and 3 mg of 4-dimethylaminopyridine (25 $\mu$mole) were added. A solution of 8.1 mg of diglycolic anhydride in dichloromethane was added to the above mixture dropwise on the ice bath under Ar gas. The mixture was stirred at room temperature for 2 h and washed with 5% citric acid 2 time and saturated sodium chloride 2 times. The organic layer was dried with sodium sulfate and solvent was removed. The product was purified by silica chromatography and appropriate fractions were combined. Solvent was removed and the product was dried under vacuum.

Synthesis of Compound 7 (Table II)

2 mg of ethanolamine was dissolved in DMF. A DMF solution of 38 mg Compound 6 ($\mu$mole), 2 mg of 1-hydroxybenzotriazol (15 $\mu$mole), 5.7 mg of (2-(1H-benzotriazol-1-yl)-1,1,3,3-tetramethyluronium hexafluorophosphate (HBTU) (30 $\mu$mole), and 5.8 mg of diisopropylethylamine (45 $\mu$mole) was added dropwise under Ar gas while stirring. The mixture was stirred for 4 h at room temperature. The solvent then was evaporated and dichloromethane was added to dissolve. The product was purified by silica gel chromatography. Appropriate fractions were combined and solvent was removed under reduced pressure. The product was dried under vacuum.

Synthesis of Compound 8 (Table II)

26 mg of Compound 7 (20 $\mu$mole) and 2 mg of tetrazole were dissolved in dichloromethane. 8 mg of 2-cyanoethyl-N,N,N',N'-tetraisopropyl phosphoramidite was added slowly under Ar gas while stirring and the mixture was stirred another hour at room temperature. Load the mixture onto silica column for purification. Appropriate fractions were pooled and dried under reduced pressure.

Synthesis of Compound 9 (Table I)

57 mg of Compound 5 and 4.5 mg of tetrazole were dissolved in dichloromethane. 20 mg of 2-cyanoethyl-N,N,N',N'-tetraisopropyl phosphoramidite was added slowly under Ar gas while stirring and the mixture was stirred for 1 h at room temperature. Load the mixture onto silica column for purification. Appropriate fractions were pooled and dried under reduced pressure.

Synthesis of Compound 10 (Table II)

2 g of CPG (500 A, 50 $\mu$mole/g) (100 $\mu$mole) was suspended in DMF. A DMF solution of 252 mg of Compound 6 (200 $\mu$mole), 28 mg of 1-hydroxybenzotriazol (50 $\mu$mole), 80 mg of (2-(1H-benzotriazol-1-yl)-1,1,3,3-tetramethyluronium hexafluorophosphate (100 $\mu$mole), and 44 mg of diisopropylethylamine (150 $\mu$mole) were added. The mixture was shaken at room temperature for 4 h and then washed with DMF 2 times, acetonitrile 2 times and dichloromethane 2 times. The support was then dried and capped with 10% acetic anhydride/lutidine in THF and 16% 1-methylimidazol in THF at room temperature for 4 h and then washed with acetonitrile and dichloromethane and dried under vacuum.

Synthesis of Compound 11 (Table III)

4.3 g of 1,3,5 cyclohexane tricarboxylic acid (20 mmole) was dissolved in DMF. A DMF solution of 8 g of 6-amino-1-hexanol-DMT (19 mmole), 1.35 g of 1-hydroxybenzotriazol (10 mmole), 3.79 g of (2-(1H-benzotriazol-1-yl)-1,1,3,3-tetramethyluronium hexafluorophosphate (HBTU) (20 mmole), and 3.88 g of diisopropylethylamine (30 mmole) was added dropwise under Ar gas while stirring. The mixture was stirred for 4 h at room temperature. The solvent then was evaporated and dichloromethane was added to dissolve. The product was purified by silica gel chromatography. Appropriate fractions were combined and solvent was removed under reduced pressure. The product was dried under vacuum.

Synthesis of Compound 12 (Table III)

4 g of 11 was dissolved in acetonitrile and 0.5 g of 30% TCA was added. The mixture was stirred at room temperature for 1 h and solvent was removed. The product was dissolved in dichloromethane and purified on silica gel chromatography. Appropriate fractions were combined and solvent was removed under reduced pressure. The product was dried under vacuum.

Synthesis of Compound 13 (Table III)

3.2 g of Compound 12 (10 mmole) was dissolved in DMF. A DMF solution of 3.04 g of Fmoc-1,6-hexanediamine (10 mmole), 0.68 g of 1-hydroxybenzotriazol (5 mmole), 1.89 g of (2-(1H-benzotriazol-1-yl)-1,1,3,3-tetramethyluronium hexafluorophosphate (10 mmole), and 1.94 g of diisopropylethylamine (15 mmole) was added dropwise under Ar gas while stirring. The mixture was stirred for 4 h at room temperature. The solvent then was evaporated and dichloromethane was added to dissolve. The product was purified by silica gel chromatography. Appropriate fractions were combined and solvent was removed under reduced pressure. The product was dried under vacuum.

Synthesis of Compound 14 (Table III)

1.1 g of Compound 13 (1 mmole) and 82 mg of tetrazole (1.2 mmole) were dissolved in dichloromethane. 0.4 ml of 2-cyanoethyl-N,N,N',N'-tetraisopropyl phosphoramidite (1 mmole) was added slowly under Ar gas while stirring and the mixture was stirred for 1 h at room temperature. Load the mixture onto silica column for purification. Appropriate fractions were pooled and dried under reduced pressure.

Synthesis of Compound 15 (Table IV)

3.2 g of Compound 12 (10 mmole) was dissolved in DMF. A DMF solution of 2.3 g of LEV-6-amino-1-hexanol (10 mmole), 0.68 g of 1-hydroxybenzotriazol (5 mmole), 1.89 g of (2-(1H-benzotriazol-1-yl)-1,1,3,3-tetramethyluronium hexafluorophosphate (10 mmole), and 1.94 g of diisopropylethylamine (15 mmole) was added dropwise under Ar gas while stirring. The mixture was stirred for 4 h at room temperature. The solvent then was evaporated and dichloromethane was added to dissolve. The product was purified by silica gel chromatography. Appropriate fractions were combined and solvent was removed under reduced pressure. The product was dried under vacuum.

Synthesis of Compound 16 (Table IV)

5.5 g of Compound 15 (10 mmole) was dissolved in DMF. A DMF solution of 4.2 g of 6-amino-1-hexanol-DMT (10 mmole), 0.68 g of 1-hydroxybenzotriazol (5 mmole), 1.89 g of (2-(1H-benzotriazol-1-yl)-1,1,3,3-tetramethyluronium hexafluorophosphate (10 mmole), and 1.94 g of diisopropylethylamine (15 mmole) was added dropwise under Ar gas while stirring. The mixture was stirred for 4 h at room temperature. The solvent then was evaporated and dichloromethane was added to dissolve. The product was purified by silica gel chromatography. Appropriate fractions were combined and solvent was removed under reduced pressure. The product was dried under vacuum.

Synthesis of Compound 17 (Table IV)

1.9 g of Compound 16 (2 mmole) and 0.18 g of tetrazole were dissolved in dichloromethane. 0.8 ml of 2-cyanoethyl-N,N,N',N'-tetraisopropyl phosphoramidite was added slowly under Ar gas while stirring and the mixture was stirred another hour at room temperature. Load the mixture onto silica column for purification. Appropriate fractions were pooled and dried under reduced pressure.

Synthesis of Compound 18 (Table IV)

4.9 g of Compound 17 (5 mmole) was dissolved in dichloromethane and 0.6 g of triethylamine (6 mmole) and 0.3 g of 4-dimethylaminopyridine (2.5 mmole) were added. A solution of 0.7 g of diglycolic anhydride in dichloromethane was added to the above mixture dropwise on the ice bath under Ar gas while stirring. The mixture was stirred at room temperature for 2 h and washed with 5% citric acid 2 time and saturated sodium chloride 2. The organic layer was dried with sodium sulfate and solvent was removed. The product was purified by silica chromatography and appropriated fractions were combined. Solvent was removed and the product was dried under vacuum.

Synthesis of Compound 19 (Table IV)

2 g of CPG (500 A, 50 $\mu$mole/g) (100 $\mu$mole) was suspended in DMF. A DMF solution of 121 mg of Compound 18 (200 $\mu$mole), 28 mg of 1-hydroxybenzotriazol (50 $\mu$mole), 80 mg of (2-(1H-benzotriazol-1-yl)-1,1,3,3-tetramethyluronium hexafluorophosphate (100 $\mu$mole), and 44 mg of diisopropylethylamine (150 $\mu$mole) were added. The mixture was shaken at room temperature for 4 h and then washed with DMF 2 times, acetonitrile 2 times and dichloromethane 2 times. The support was then dried and capped with 10% acetic anhydride/lutidine in THF and 16% 1-methylimidazol in THF at room temperature for 4 h and then washed with acetonitrile and dichloromethane and dried under vacuum.

Synthesis of Compound 20 (Table III)

4.9 g of Compound 13 (5 mmole) was dissolved in dichloromethane and 0.6 g of triethylamine (6 mmole) and 0.3 g of 4-dimethylaminopyridine (2.5 mmole) were added. A solution of 0.7 g of diglycolic anhydride in dichloromethane was added to the above mixture dropwise on the ice bath under Ar gas while stirring. The mixture was stirred at room temperature for 2 h and washed with 5% citric acid 2 time and saturated sodium chloride 2. The organic layer was dried with sodium sulfate and solvent was removed. The product was purified by silica chromatography and appropriated fractions were combined. Solvent was removed and the product was dried under vacuum.

Synthesis of Compound 21 (Table III)

2 g of CPG (500 A, 50 $\mu$mole/g) (100 $\mu$mole) was suspended in DMF. A DMF solution of 121 mg of Compound 20 (200 µmole), 28 mg of 1-hydroxybenzotriazol (50 µmole), 80 mg of (2-(1H-benzotriazol-1-yl)-1,1,3,3-tetramethyluronium hexafluorophosphate (100 µmole), and 44 mg of diisopropylethylamine (150 µmole) were added. The mixture was shaken at room temperature for 4 h and then washed with DMF 2 times, acetonitrile 2 times and dichloromethane 2 times. The support was then dried and capped with 10% acetic anhydride/lutidine in THF and 16% 1-methylimidazol in THF at room temperature for 4 h and then washed with acetonitrile and dichloromethane and dried under vacuum.

Synthesis of Compound 22 (Table V)

3.2 g of Compound 12 (10 mmole) was dissolved in DMF. A DMF solution of 6.7 g of Fmoc-1,6-hexanediamine (22 mmole), 0.68 g of 1-hydroxybenzotriazol (5 mmole), 1.89 g of (2-(1H-benzotriazol-1-yl)-1,1,3,3-tetramethyluronium hexafluorophosphate (10 mmole), and 1.94 g of diisopropylethylamine (15 mmole) was added dropwise under Ar gas while stirring. The mixture was stirred for 4 h at room temperature. The solvent then was evaporated and Dichloromethane was added to dissolve. The product was purified by silica gel chromatography. Appropriate fractions were combined and solvent was removed under reduced pressure. The product was dried under vacuum.

Synthesis of Compound 23 (Table V)

5 g of Compound 22 was dissolved in 20% piperidine in DMF. The solution was stirred at room temperature for 2 h. The solvent was then removed and the product was dissolved in Dichloromethane and purified on silica chromatography. Appropriate fractions were pooled and dried under reduced pressure.

Synthesis of Compound 24 (Table V)

1.8 g of Compound 22 (2 mmole) and 0.18 g of tetrazole (2.5 mmole) were dissolved in Dichloromethane. 0.8 ml of 2-cyanoethyl-N,N,N',N'-tetraisopropyl phosphoramidite (2 mmole) was added slowly under Ar gas and the mixture was stirred for 1 h at room temperature. Load the mixture onto silica column for purification. Appropriate fractions were pooled and dried under reduced pressure.

Synthesis of Compound 25 (Table V)

72 mg of Compound 22 (0.1 mmole) was dissolved in DMF. 53 mg of FAM-NHS (carboxyfluorescein—N-hydroxysuccinimide) ester (0.1 mmole) and 30 mg of triethylamine (0.3 mmole) were added. The mixture was stirred at room temperature for 16 h and the solvent was removed. The product was dissolved in Dichloromethane and purified on silica chromatography. Appropriate fractions were pooled and dried under reduced pressure.

Synthesis of Compound 26 (Table V)

105 mg of Compound 25 (0.1 mmole) was dissolved in DMF. 53 mg of TMR-NHS ester (0.1 mmole) and 30 mg of triethylamine (0.3 mmole) were added. The mixture was stirred at room temperature for 16 h and the solvent was removed. The product was dissolved in Dichloromethane and purified on silica chromatography. Appropriate fractions were pooled and dried under reduced pressure.

Synthesis of Compound 27 (Table V)

1.9 g of Compound 26 (2 mmole) and 0.18 g of tetrazole were dissolved in Dichloromethane. 0.8 ml of 2-cyanoethyl-N,N,N',N'-tetraisopropyl phosphoramidite was added slowly under Ar gas while stirring and the mixture was stirred another hour at room temperature. Load the mixture onto silica column for purification. Appropriate fractions were pooled and dried under reduced pressure.

Synthesis of Compound 28 (Table VI)

11.7 g of 6-amino-1-hexanol (100 mmole) was dissolved in DMF. 35.4 g of Fmoc-OSU (110 mmole) was added along with 20 ml pyridine. The mixture was stirred overnight at room temperature. The solvent then was evaporated and Dichloromethane was added to dissolve. The product was then washed with 5% citric acid 2 times and saturated brine once. The solution was then dried and filtered and solvent was removed. The product was washed with ether and dried.

Synthesis of Compound 29 (Table VI)

3.4 g of Compound 28 was dissolve in pyridine and was added with 3.4 g DMT-Cl solution in pyridine dropwise under Ar gas flow while stirring. The mixture was stirred for 48 h at room temperature. The solvent was removed under reduced pressure and the product was dissolved in Dichloromethane. The product then was purified by silica gel chromatography. Appropriate fractions were combined and solvent was removed under reduced pressure. The product was dried under vacuum.

Synthesis of Compound 30 (Table VI)

5 g of Compound 29 was dissolved in 20% piperidine in DMF. The solution was stirred at room temperature for 2 h. The solvent was then removed and the product was dissolved in Dichloromethane and purified on silica chromatography. Appropriated fractions were pooled and dried under reduced pressure.

Synthesis of Compound 31 (Table VI)

3.3 g of Fmoc-serine (10 mmole) was dissolved in DMF. A DMF solution of 4.2 g of Compound 30 (10 mmole), 0.68 g of 1-hydroxybenzotriazol (5 mmole), 1.89 g of (2-(1H-benzotriazol-1-yl)-1,1,3,3-tetramethyluronium hexafluorophosphate (10 mmole), and 1.94 g of diisopropylethylamine (15 mmole) was added dropwise under Ar gas while stirring. The mixture was stirred for 4 h at room temperature. The solvent then was evaporated and Dichloromethane was added to dissolve. The product was purified by silica gel chromatography. Appropriate fractions were combined and solvent was removed under reduced pressure. The product was dried under vacuum.

Synthesis of Compound 32 (Table VI)

5 g of Compound 31 was dissolved in 20% piperidine in DMF. The solution was stirred at room temperature for 2 h. The solvent was then removed and the product was dissolved in Dichloromethane and purified on silica chromatography. Appropriate fractions were pooled and dried under reduced pressure.

Synthesis of Compound 33 (Table VI)

51 mg of Compound 32 (0.1 mmole) was dissolved in DMF. 53 mg of TMR-NHS ester (0.1 mmole) and 30 mg of triethylamine (0.3 mmole) were added. The mixture was stirred at room temperature for 16 h and the solvent was removed. The product was dissolved in Dichloromethane and purified on silica chromatography. Appropriate fractions were pooled and dried under reduced pressure.

Synthesis of Compound 34 (Table VI)

49 mg of Compound 33 (50 µmole) was dissolved in Dichloromethane and 4.5 mg of triethylamine (45 µmole) and 3 mg of 4-dimethylaminopyridine (25 µmole) were added. A solution of 8.1 mg of diglycolic anhydride in dicholoromethane was added to the above mixture dropwise on the ice bath under Ar gas. The mixture was stirred at room temperature for 2 h and washed with 5% citric acid 2 time and saturated sodium chloride 2 times. The organic layer was dried with sodium sulfate and solvent was removed. The product was purified by silica chromatography and appropriate fractions were combined. Solvent was removed and the product was dried under vacuum.

Synthesis of Compound 35 (Table VI)

2 mg of ethanolamine was dissolved in DMF. A DMF solution of 32 mg 34 (30 µmole), 2 mg of 1-hydroxybenzotriazol (15 µmole), 5.7 mg of (2-(1H-benzotriazol-1-yl)-1,1,3,3-tetramethyluronium hexafluorophosphate (30 µmole), and 5.8 mg of diisopropylethylamine (45 µmole) was added dropwise under Ar gas while stirring. The mixture was stirred for 4 h at room temperature. The solvent then was evaporated and Dichloromethane was added to dissolve. The product was purified by silica gel chromatography. Appropriate fractions were combined and solvent was removed under reduced pressure. The product was dried under vacuum.

Synthesis of Compound 36 (Table VI)

22 mg of Compound 34 (20 µmole) and 2 mg of tetrazole were dissolved in dichloromethane. 8 µl of 2-cyanoethyl-N,N,N',N'-tetraisopropyl phosphoramidite was added slowly under Ar gas while stirring and the mixture was stirred another hour at room temperature. Load the mixture onto silica column for purification. Appropriate fractions were pooled and dried under reduced pressure.

Synthesis of Compound 37 (Table VI)

49 mg of Compound 33 and 4.5 mg of tetrazole were dissolved in dichloromethane. 20 mg of 2-cyanoethyl-N,N,N',N'-tetraisopropyl phosphoramidite was added slowly under Ar gas while stirring and the mixture was stirred for 1 h at room temperature. Load the mixture onto silica column for purification. Appropriate fractions were pooled and dried under reduced pressure.

Synthesis of Compound 38 (Table VI)

2 g of CPG (500 A, 50 µmole/g) (100 µmole) was suspended in DMF. A DMF solution of 200 mg of Compound 34 (200 µmole), 28 mg of 1-hydroxybenzotriazol (50 µmole), 80 mg of (2-(1H-benzotriazol-1-yl)-1,1,3,3-tetramethyluronium hexafluorophosphate (100 µmole), and 44 mg of diisopropylethylamine (150 µmole) were added. The mixture was shaken at room temperature for 4 h and then washed with DMF 2 times, acetonitrile 2 times and Dichloromethane 2 times. The support was then dried and capped with 10% acetic anhydride/lutidine in THF and 16% 1-methylimidazol in THF at room temperature for 4 h and then washed with acetonitrile and Dichloromethane and dried under vacuum.

Synthesis of Compound 39 (Table VII)

0.37 g of serinol (20 mmole) was dissolved in DMF. A DMF solution of 4.2 g of trifluoroacetic anhydride (20 mmole), 1.35 g of 1-hydroxybenzotriazol (10 mmole), 3.79 g of (2-(1H-benzotriazol-1-yl)-1,1,3,3-tetramethyluronium hexafluorophosphate (20 mmole), and 3.88 g of diisopropylethylamine (30 mmole) was added dropwise under Ar gas while stirring. The mixture was stirred for 4 h at room temperature. The solvent then was evaporated and Dichloromethane was added to dissolve. The product was purified by silica gel chromatography. Appropriate fractions were combined and solvent was removed under reduced pressure. The product was dried under vacuum.

Synthesis of Compound 40 (Table VII)

2.81 g of Compound 39 (7 mmole) was dissolved in pyridine and was added with 2.13 g of DMT-Cl solution in pyridine dropwise under Ar gas flow. The mixture was stirred for 48 h at room temperature. The solvent was removed under reduced pressure and the product was dissolved in Dichloromethane. The product then was purified by silica gel chromatography. Appropriate fractions were combined and solvent was removed under reduced pressure. The product was dried under vacuum.

Synthesis of Compound 41 (Table VII)

2.45 g of Compound 40 (5 mmole) was dissolved in Dichloromethane and 0.6 g of triethylamine (6 mmole) and 0.3 g of 4-dimethylaminopyridine (2.5 mmole) were added. A solution of 0.7 g of diglycolic anhydride in Dichloromethane was added to the above mixture dropwise on the ice bath under Ar gas while stirring. The mixture was stirred at room temperature for 2 h and washed with 5% citric acid 2 time and saturated sodium chloride 2. The organic layer was dried with sodium sulfate and solvent was removed. The product was purified by silica chromatography and appropriated fractions were combined. Solvent was removed and the product was dried under vacuum.

Synthesis of Compound 42 (Table VII)

2 g of CPG (500 A, 50 µmole/g) (100 µmole) was suspended in DMF. A DMF solution of 121 mg of Compound 41 (200 µmole), 28 mg of 1-hydroxybenzotriazol (50 µmole), 80 mg of (2-(1H-benzotriazol-1-yl)-1,1,3,3-tetramethyluronium hexafluorophosphate (100 µmole), and 44 mg of diisopropylethylamine (150 µmole) were added. The mixture was shaken at room temperature for 4 h and then washed with DMF 2 times, acetonitrile 2 times and Dichloromethane 2 times. The support was then dried and capped with 10% acetic anhydride/lutidine in THF and 16% 1-methylimidazol in THF at room temperature for 4 h and then washed with acetonitrile and Dichloromethane and dried under vacuum.

Synthesis of Compound 43 (Table VII)

200 mg of ethanolamine was dissolved in DMF. A DMF solution of 1.8 g 42 (3 mmole), 0.2 g of 1-hydroxybenzotriazol (1.5 mmole), 0.57 g of (2-(1H-benzotriazol-1-yl)-1,1,3,3-tetramethyluronium hexafluorophosphate (3 mmole), and 0.58 g of diisopropylethylamine (4.5 mmole) was added dropwise under Ar gas while stirring. The mixture was stirred for 4 h at room temperature. The solvent then was evaporated and Dichloromethane was added to dissolve. The product was purified by silica gel chromatography. Appropriate fractions were combined and solvent was removed under reduced pressure. The product was dried under vacuum.

Synthesis of Compound 44 (Table VII)

1.3 g of Compound 44 (2 mmole) and 0.2 g of tetrazole were dissolved in Dichloromethane. 0.8 ml of 2-cyanoethyl- N,N,N',N'-tetraisopropyl phosphoramidite was added slowly under Ar gas while stirring and the mixture was stirred another hour at room temperature. Load the mixture onto silica column for purification. Appropriate fractions were pooled and dried under reduced pressure.

Synthesis of Compound 45 (Table VIII)

2.74 g of 5'-DMT-deoxyribothymidine (5 mmole) was dissolved in Dichloromethane and 0.6 g of triethylamine (6 mmole) and 0.3 g of 4-dimethylaminopyridine (2.5 mmole) were added. A solution of 0.7 g of diglycolic anhydride in Dichloromethane was added to the above mixture dropwise on the ice bath under Ar gas while stirring. The mixture was stirred at room temperature for 2 h and washed with 5% citric acid 2 time and saturated sodium chloride 2. The organic layer was dried with sodium sulfate and solvent was removed. The product was purified by silica chromatography and appropriated fractions were combined. Solvent was removed and the product was dried under vacuum.

Synthesis of Compound 46 (Table VIII)

2 g of CPG (500 A, 50 μmole/g) (100 μmole) was suspended in DMF. A DMF solution of 133 mg of Compound 40 (200 μmole), 28 mg of 1-hydroxybenzotriazol (50 μmole), 80 mg of (2-(1H-benzotriazol-1-yl)-1,1,3,3-tetramethyluronium hexafluorophosphate (100 μmole), and 44 mg of diisopropylethylamine (150 μmole) were added. The mixture was shaken at room temperature for 4 h and then washed with DMF 2 times, Acetonitrile 2 times and Dichloromethane 2 times. The support was then dried and capped with 10% acetic anhydride/lutidine in THF and 16% 1-methylimidazol in THF at room temperature for 4 h and then washed with acetonitrile and Dichloromethane and dried under vacuum.

Synthesis of Compound 47 (Table VIII)

200 mg of ethanolamine was dissolved in DMF. A DMF solution of 2 g Compound 46 (3 mmole), 0.2 g of 1-hydroxybenzotriazol (1.5 mmole), 0.57 g of (2-(1H-benzotriazol-1-yl)-1,1,3,3-tetramethyluronium hexafluorophosphate (3 mmole), and 0.58 g of diisopropylethylamine (4.5 mmole) was added dropwise under Ar gas while stirring. The mixture was stirred for 4 h at room temperature. The solvent then was evaporated and Dichloromethane was added to dissolve. The product was purified by silica gel chromatography. Appropriate fractions were combined and solvent was removed under reduced pressure. The product was dried under vacuum.

Synthesis of Compound 48 (Table VIII)

1.4 g of Compound 47 (2 mmole) and 0.2 g of tetrazole were dissolved in Dichloromethane. 0.8 ml of 2-cyanoethyl-N,N,N',N'-tetraisopropyl phosphoramidite was added slowly under Ar gas while stirring and the mixture was stirred another hour at room temperature. Load the mixture onto silica column for purification. Appropriate fractions were pooled and dried under reduced pressure.

Synthesis of Compound 49 (Table IX)

1 g of amino-FAM was dissolved in DMF. A DMF solution of 0.9 g of Fmoc-serine (3 mmole), 0.2 g of 1-hydroxybenzotriazol (1.5 mmole), 0.57 g of (2-(1H-benzotriazol-1-yl)-1,1,3,3-tetramethyluronium hexafluorophosphate (3 mmole), and 0.58 g of diisopropylethylamine (4.5 mmole) was added dropwise under Ar gas while stirring. The mixture was stirred for 4 h at room temperature. The solvent then was evaporated and Dichloromethane was added to dissolve. The product was purified by silica gel chromatography. Appropriate fractions were combined and solvent was removed under reduced pressure. The product was dried under vacuum.

Synthesis of Compound 50 (Table IX)

1 g of Compound 49 was dissolved in 20% piperidine in DMF. The solution was stirred at room temperature for 16 h and the solvent was removed. The product was dissolved in dichloromethane and purified on silica chromatography. Appropriate fractions were pooled and dried under reduced pressure.

Synthesis of Compound 51 (Table IX)

600 mg of Compound 50 (1 mmole) was dissolved in DMF. 530 mg of TMR-NHS ester (1 mmole) and 300 mg of triethylamine (3 mmole) were added. The mixture was stirred at room temperature for 16 h and the solvent was removed. The product was dissolved in dichloromethane and purified on silica chromatography. Appropriate fractions were pooled and dried under reduced pressure.

Synthesis of Compound 52 (Table IX)

1.1 g of Compound 51 (1 mmole) and 0.1 g of tetrazole were dissolved in dichloromethane. 0.4 ml of 2-cyanoethyl-N,N,N',N'-tetraisopropyl phosphoramidite was added slowly under Ar while stirring and the mixture was stirred another hour at room temperature. Load the mixture onto silica column for purification. Appropriate fractions were pooled and dried under reduced pressure.

Synthesis of Compound 53 (Table X)

21 mg of 3,5-diamino phenyl alcohol (0.1 mmole) was dissolved in DMF. 53 mg of FAM-NHS ester (0.1 mmole) and 30 mg of triethylamine (0.3 mmole) were added. The mixture was stirred at room temperature for 16 h and the solvent was removed. The product was dissolved in Dichloromethane and purified on silica chromatography. Appropriate fractions were pooled and dried under reduced pressure.

Synthesis of Compound 54 (Table X)

54 mg of Compound 53 (0.1 mmole) was dissolved in DMF. 53 mg of TMR-NHS ester (0.1 mmole) and 30 mg of triethylamine (0.3 mmole) were added. The mixture was stirred at room temperature for 16 h and the solvent was removed. The product was dissolved in Dichloromethane and purified on silica chromatography. Appropriate fractions were pooled and dried under reduced pressure.

Synthesis of Compound 55 (Table X)

1.2 g of Compound 54 (2 mmole) and 0.18 g of tetrazole were dissolved in Dichloromethane. 0.8 ml of 2-cyanoethyl-N,N,N',N'-tetraisopropyl phosphoramidite was added slowly under Ar gas while stirring and the mixture was stirred another hour at room temperature. Load the mixture onto silica column for purification. Appropriate fractions were pooled and dried under reduced pressure.

All publications and patent applications cited in this specification are herein incorporated by reference, as if each individual publication or patent application were specifically and individually indicated to be incorporated by reference.

Although the foregoing invention has been described in some detail by way of illustration and example for purposes of clarity of understanding, it will be readily apparent to those of ordinary skill in the art, in light of the teachings of this invention, that certain changes and modifications may be made thereto without departing from the spirit or scope of the appended claims.

TABLE I

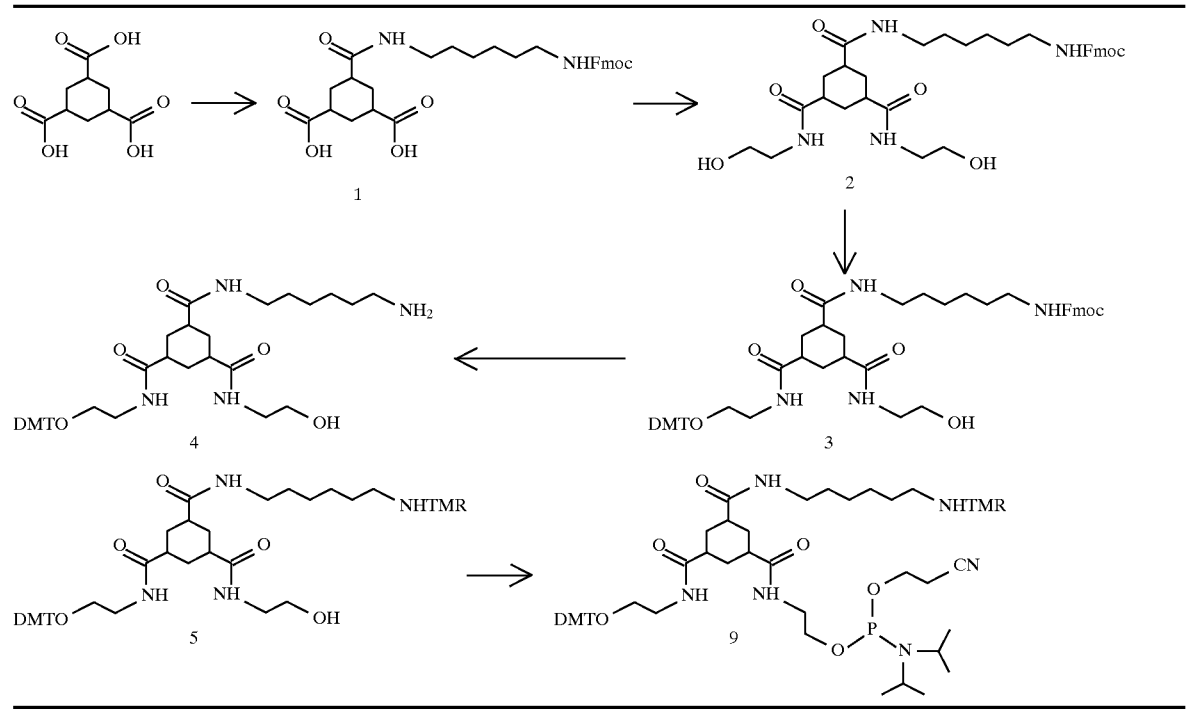

TABLE II

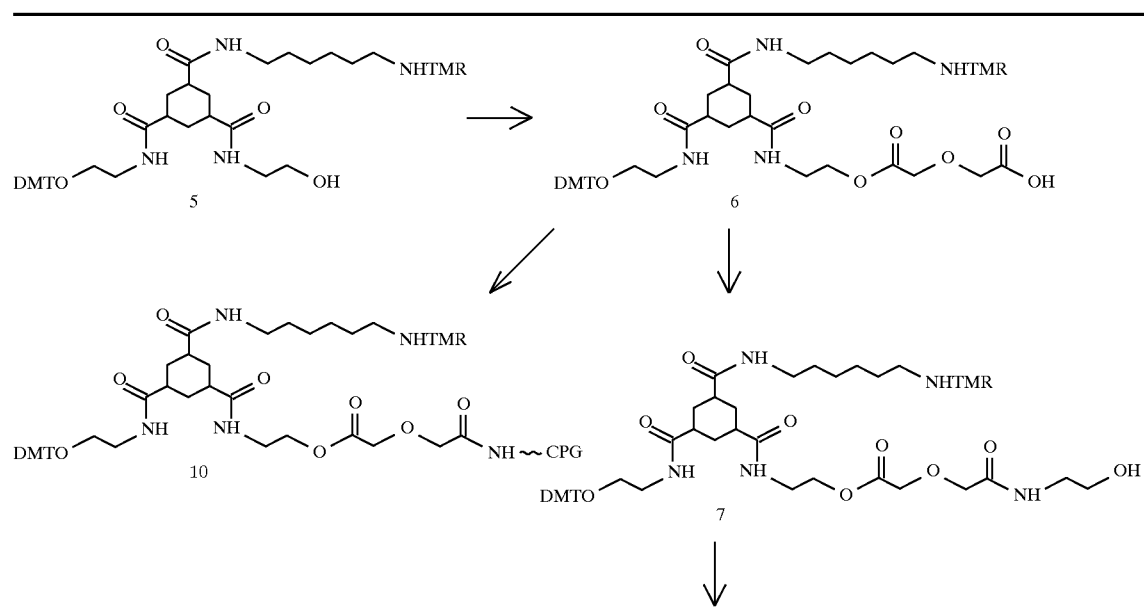

TABLE II-continued
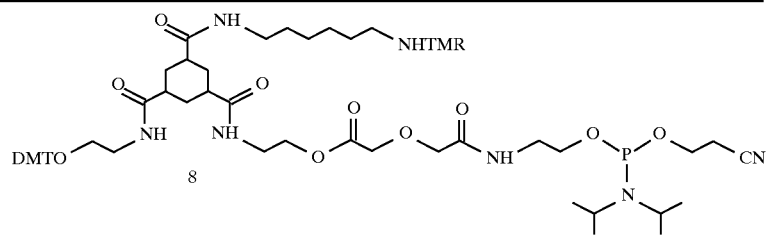
TABLE III
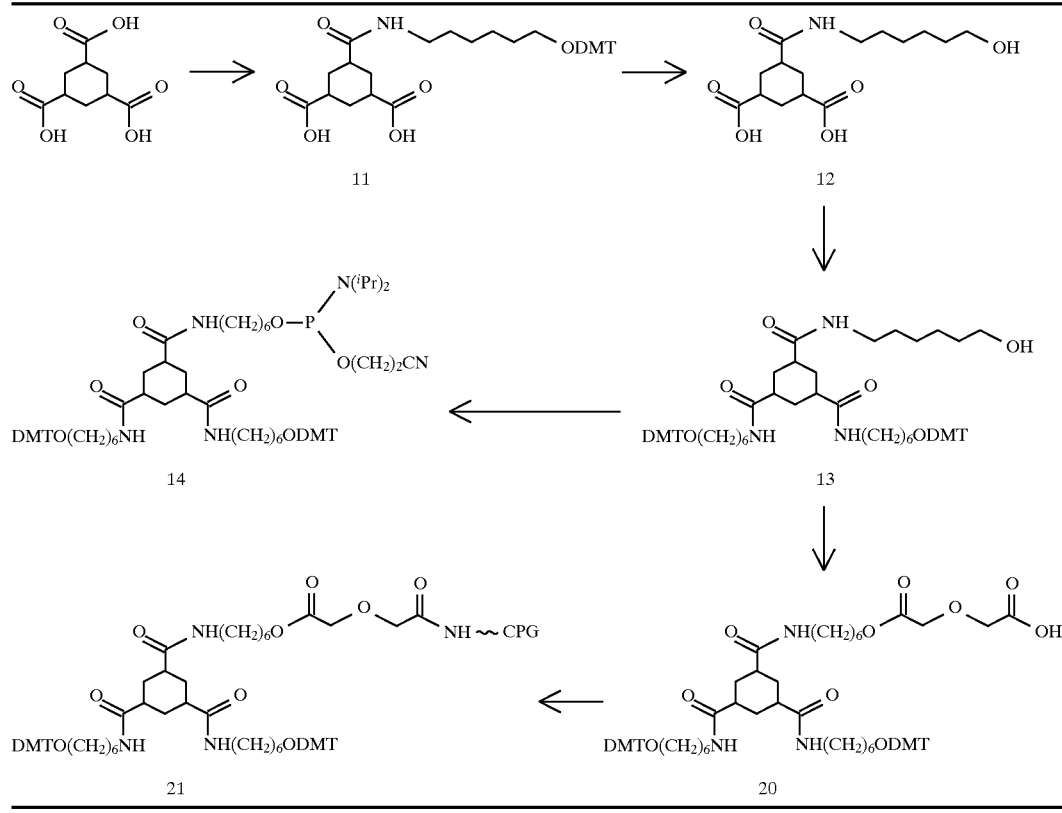
TABLE IV
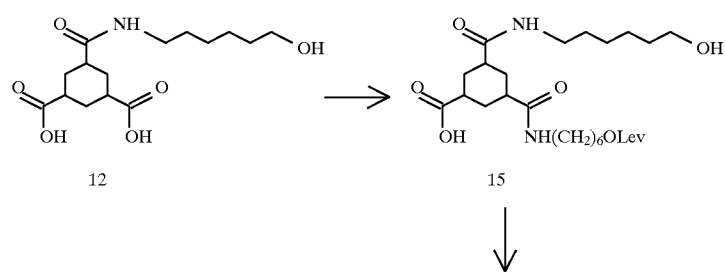

TABLE IV-continued
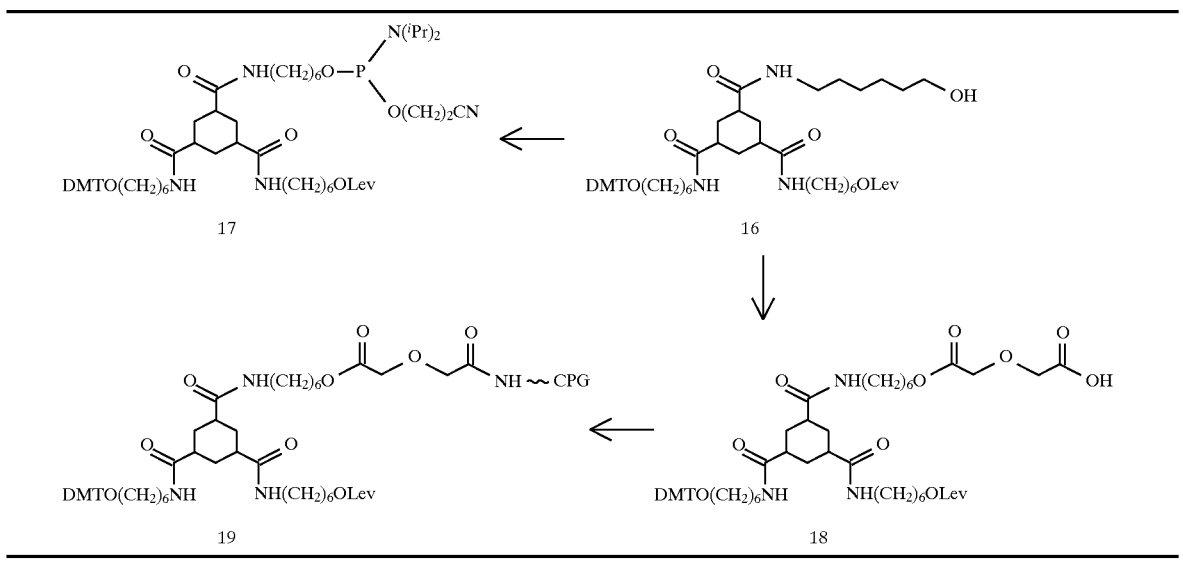
TABLE V
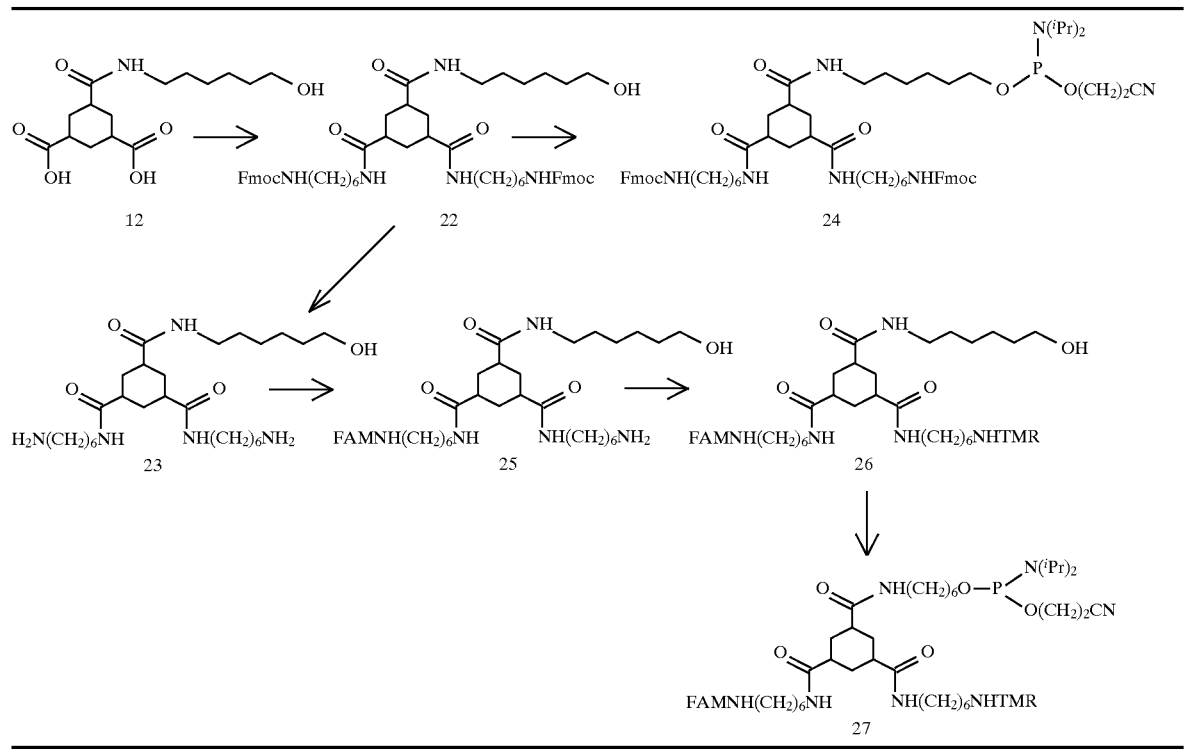
TABLE VI
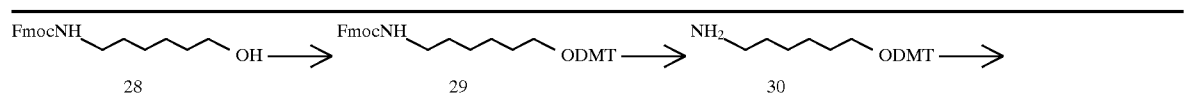

TABLE VI-continued
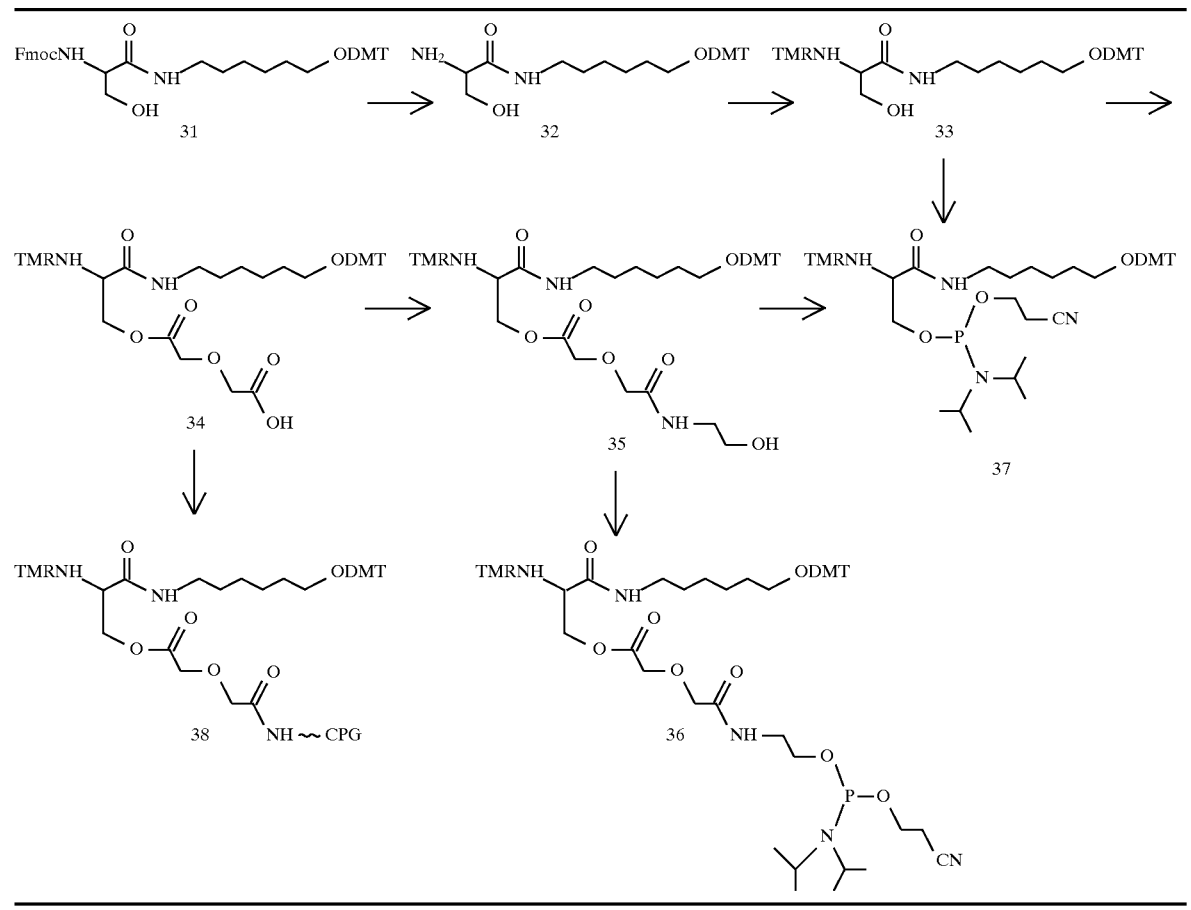
TABLE VII
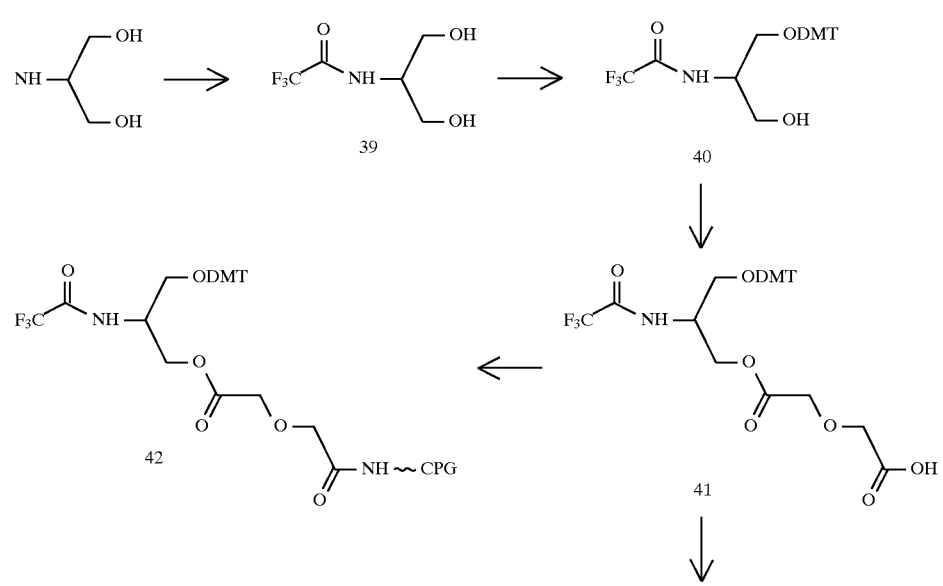

TABLE VII-continued
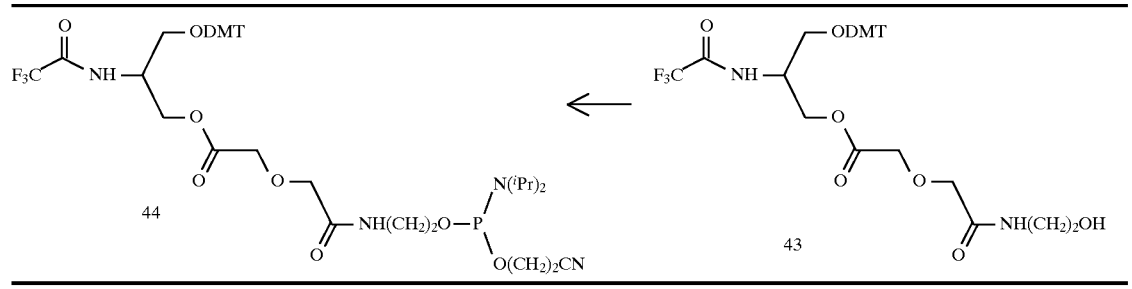
TABLE VIII
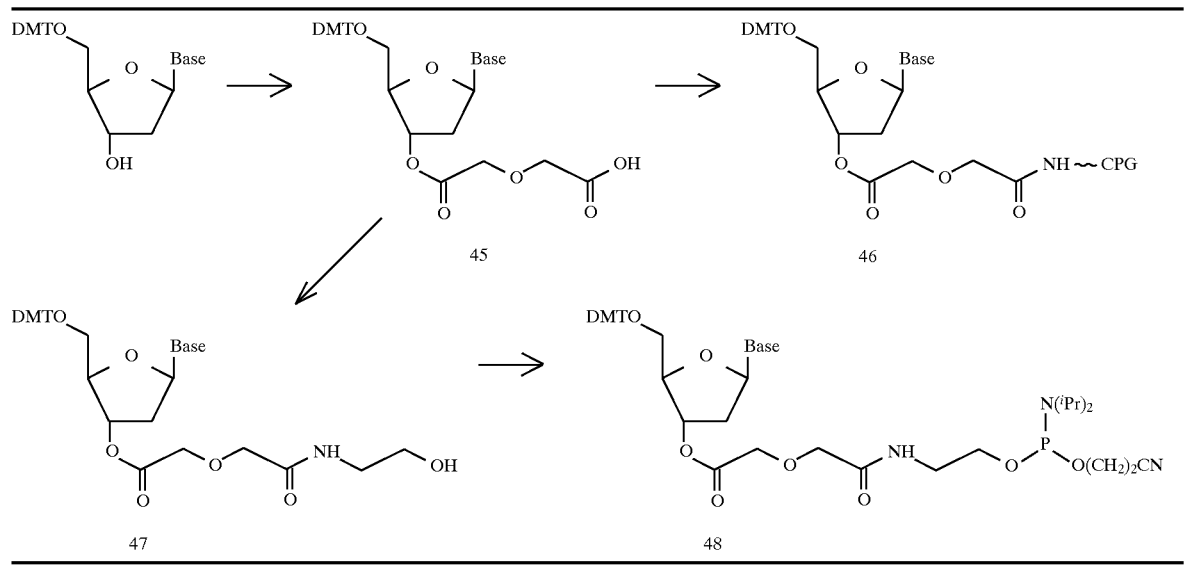
TABLE IX
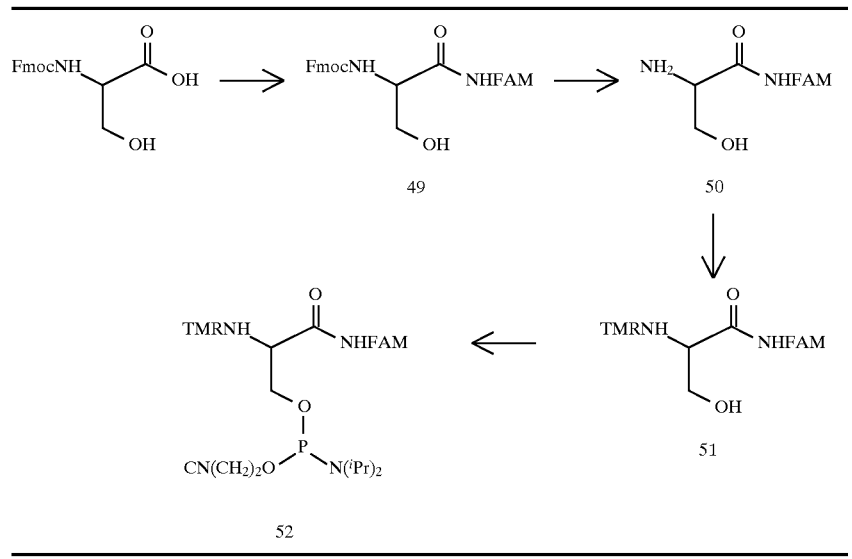

What is claimed is:

1. A compound having the structure:

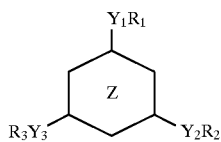

wherein:

Z is 1,3,5 tri-substituted phenyl 1,3,5 tri-substituted heterophenyl, 1,3,5 tri-substituted cyclohexyl or 1,3,5 tri-substituted heterocyclohexyl, wherein said heterophenyl and heterocyclohexyl contain a O, N or S heteroatom at at least one of positions 2, 4 and 6;

$R_1$ and $R_2$ are detectable labels or protecting groups independently selected from the group consisting of amine protecting groups and hydroxyl protecting groups; wherein the amine protecting groups are selected from the group consisting of 9-fluorenylmethyloxycarbonyl (Fmoc) and butyloxycarbonyl (BOC) and wherein the hydroxyl protecting groups are selected from the group consisting of dimethoxytrityl (DMT), monomethoxytrityl (MMT) and levulinyl (Lev);

$Y_1$, $Y_2$, and $Y_3$ are linker arms covalently linking $R_1$, $R_2$ and $R_3$, respectively, to Z, and are independently selected from the group consisting of —NH(CH$_2$)$_n$NHCO—, —O(CH$_2$)$_n$NHCO, —NHCOCH$_2$OCH$_2$COO(CH$_2$)$_2$NHCO—, —OOCCH$_2$OCH$_2$CONHO(CH$_2$)$_2$O—, —OOCCH$_2$OCH$_2$CONH—, —N—, —O—, —CONH— and —CH$_2$O—, wherein n is an integer from 0 to 8; and $R_3$ is a coupling group selected from the group consisting of phosphoramidite group, an amine group, a hydroxyl group, and a solid support.

2. A compound according to claim 1, wherein Z is 1,3,5 tri-substituted phenyl or 1,3,5 tri-substituted cyclohexyl.

3. A compound according to claim 2 selected from the group consisting of compounds 8, 9, 10, 14, 17, 19, 24, 27 and 55, below:

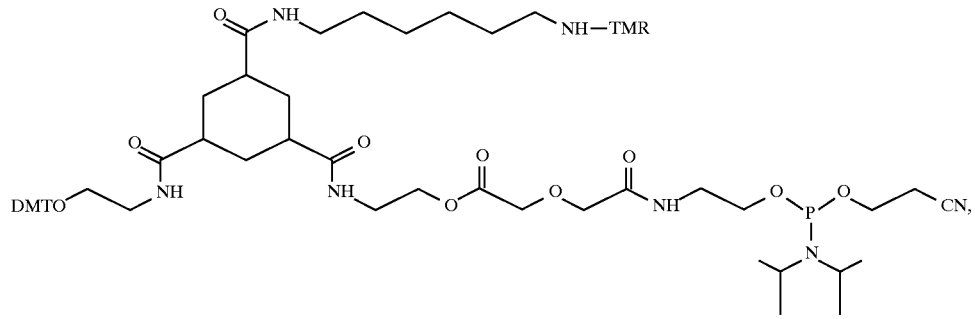

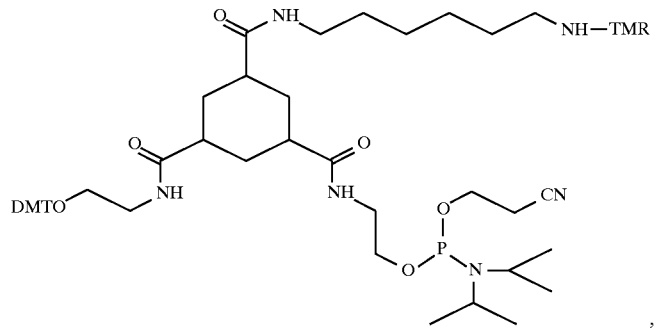

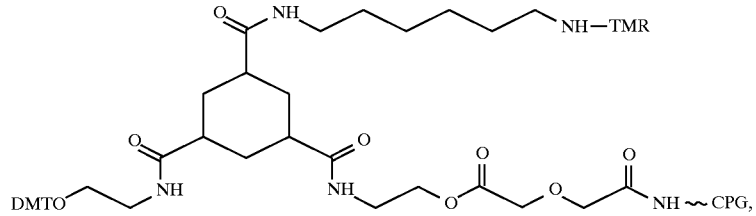

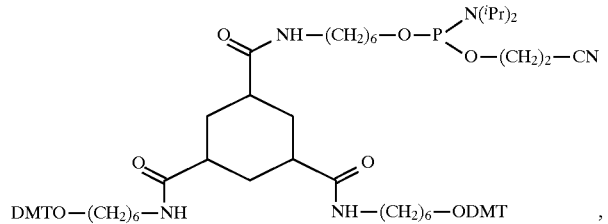

-continued

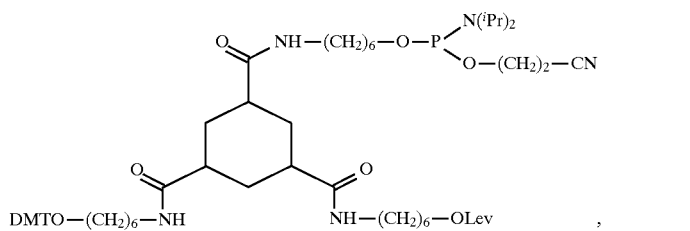
17

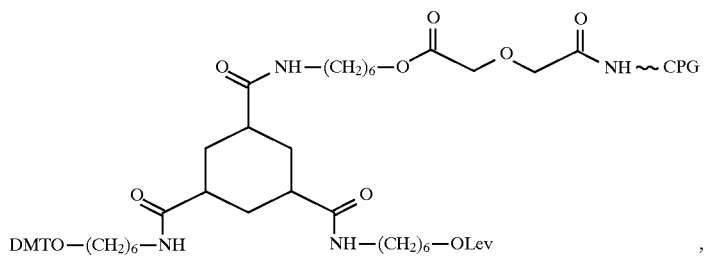
19

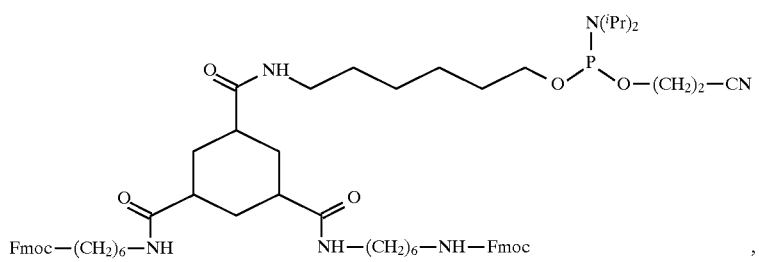
24

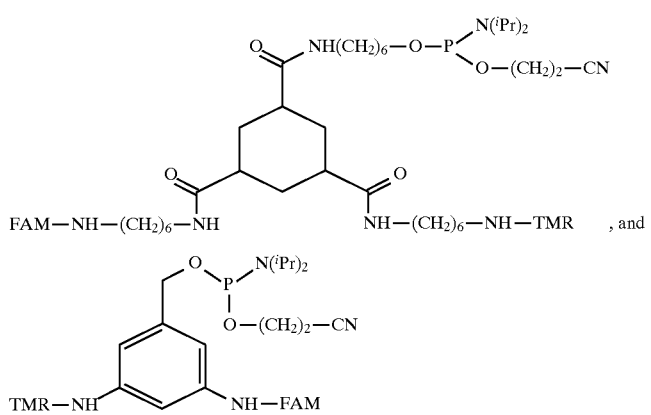
27
, and

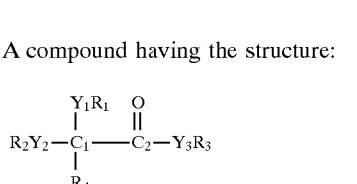
55

4. A compound having the structure:

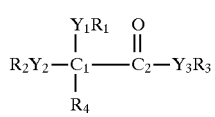

wherein $C_1$ and $C_2$ are carbon atoms;

$R_1$ and $R_2$ are detectable labels or protecting groups independently selected from the group consisting of amine protecting groups and hydroxyl protecting groups; wherein the amine protecting groups are selected from the group consisting of 9-fluorenylmethyloxycarbonyl (Fmoc) and butyloxycarbonyl (BOC) and wherein the hydroxyl protecting groups are selected from the group consisting of dimethoxytrityl (DMT), monomethoxytrityl (MMT) and levulinyl (Lev);

$Y_1$, $Y_2$, and $Y_3$ are linker arms covalently linking $R_1$, $R_2$ and $R_3$, respectively, to $C_1$, $C_1$ and $C_2$, respectively, and are independently selected from the group consisting of —NH(CH$_2$)$_n$NHCO—, —O(CH$_2$)$_n$NHCO, —NHCOCH$_2$OCH$_2$COO(CH$_2$)$_2$NHCO—, —OOCCH$_2$OCH$_2$CONHO(CH$_2$)$_2$O—, —OOCCH$_2$OCH$_2$CONH—, —N—, —O—, —CONH— and —CH$_2$O—, wherein n is an integer from 0 to 8;

$R_3$ is a coupling group selected from the group consisting of phosphoramidite group, an amine group, a hydroxyl group, and a solid support; and $R_4$ is H or lower alkyl group.

5. A compound according to claim 4 selected from the group consisting of compounds 36,

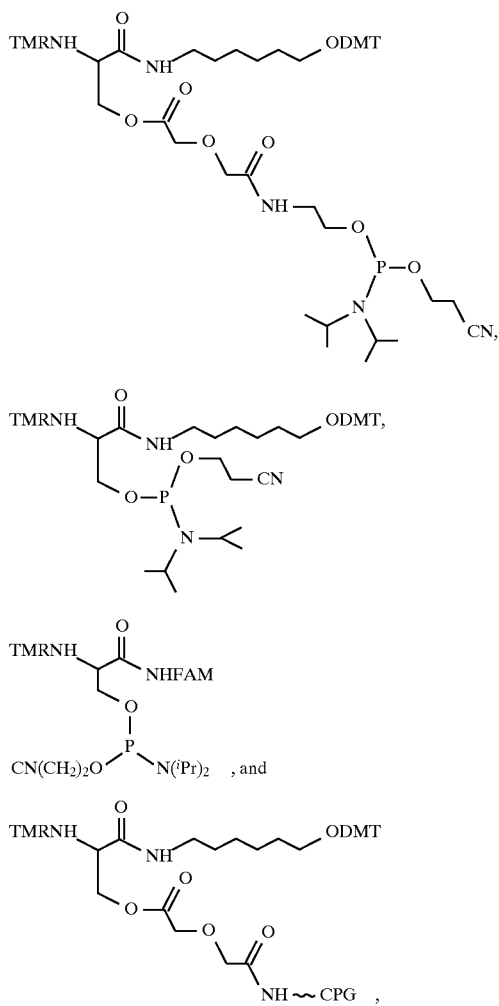

wherein DMT is dimethoxytrityl and CPG is controlled pore glass.

6. A compound selected from the group consisting of compounds 46 and 48, below:

wherein DMT is dimethoxytrityl and CPG is controlled pore glass.

7. In a method of labelling an oligonucleotide the improvement comprising reacting said oligonucleotide with the compound of claim 1.

8. In a method of labelling an oligonucleotide the improvement comprising reacting said oligonucleotide with the compound of claim 4.

9. In a method of labelling an oligonucleotide the improvement comprising reacting said oligonucleotide with the compound of claim 6.

* * * * *